(12) United States Patent
Lappalainen et al.

(10) Patent No.: US 8,486,073 B2
(45) Date of Patent: Jul. 16, 2013

(54) COATING ON A MEDICAL SUBSTRATE AND A COATED MEDICAL PRODUCT

(75) Inventors: Reijo Lappalainen, Hiltulanlahti (FI); Vesa Myllymäki, Helsinki (FI); Lasse Pulli, Helsinki (FI); Jari Ruuttu, Billnäs (FI); Juha Mäkitalo, Tammisaari (FI)

(73) Assignee: Picodeon Ltd Oy, Helsinki (FI)

( * ) Notice: Subject to any disclaimer, the term of this patent is extended or adjusted under 35 U.S.C. 154(b) by 1022 days.

(21) Appl. No.: 12/280,609

(22) PCT Filed: Feb. 23, 2007

(86) PCT No.: PCT/FI2007/050097
§ 371 (c)(1),
(2), (4) Date: Aug. 25, 2008

(87) PCT Pub. No.: WO2007/096476
PCT Pub. Date: Aug. 30, 2007

(65) Prior Publication Data
US 2009/0012523 A1    Jan. 8, 2009

(30) Foreign Application Priority Data

| Feb. 23, 2006 | (FI) | 20060177 |
| Feb. 23, 2006 | (FI) | 20060178 |
| Feb. 23, 2006 | (FI) | 20060181 |
| Feb. 23, 2006 | (FI) | 20060182 |

(51) Int. Cl.
*A61B 17/58* (2006.01)
*A61L 27/30* (2006.01)
*B23K 26/06* (2006.01)
*C23C 14/28* (2006.01)

(52) U.S. Cl.
USPC ........................ 606/76; 427/2.26

(58) Field of Classification Search
USPC .......... 606/76–78; 428/615; 427/596, 2.26, 427/2.27
See application file for complete search history.

(56) References Cited

U.S. PATENT DOCUMENTS

| 4,394,236 A | 7/1983 | Robinson |
| 4,990,163 A * | 2/1991 | Ducheyne et al. ........... 427/2.24 |

(Continued)

FOREIGN PATENT DOCUMENTS

| GB | 2 293 693 | 3/1996 |
| JP | 7070740 | 3/1995 |
| WO | 99/13127 | 3/1999 |
| WO | 03/061840 | 7/2003 |

OTHER PUBLICATIONS

Kreutz, E. W. et al., "Large area pulsed laser deposition of ceramic films", Surf. coat. technol., Dec. 1997, Abstract.

(Continued)

*Primary Examiner* — Kevin T Truong
*Assistant Examiner* — Christopher Beccia
(74) *Attorney, Agent, or Firm* — Young & Thompson

(57) ABSTRACT

The invention relates in general level to a method for coating articulating surfaces of medical products. The invention also relates to coated medical products manufactured by the method. The coating is carried out by employing ultra short pulsed laser deposition wherein pulsed laser beam is preferably scanned with a rotating optical scanner including at least one mirror for reflecting the laser beam. The invention has several both industrially and qualitatively advantageous effects such as high coating production rate, excellent coating properties and overall low manufacturing costs.

9 Claims, 10 Drawing Sheets

U.S. PATENT DOCUMENTS

Figure 3:
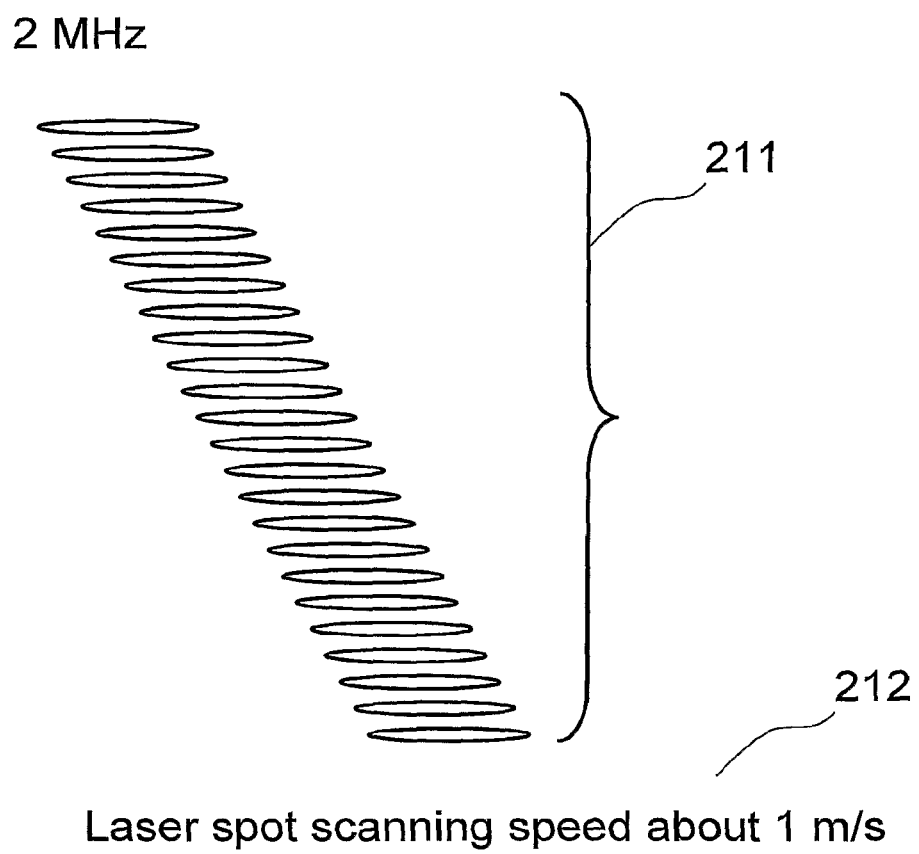

| | | | |
|---|---|---|---|
| 5,242,706 A * | 9/1993 | Cotell et al. | 427/2.27 |
| 5,490,912 A * | 2/1996 | Warner et al. | 204/298.02 |
| 5,760,366 A | 6/1998 | Haruta et al. | |
| 6,270,861 B1 * | 8/2001 | Mashburn | 427/561 |
| 6,312,768 B1 * | 11/2001 | Rode et al. | 427/596 |
| 6,748,959 B1 * | 6/2004 | Kashiwaya et al. | 134/1.1 |
| 6,984,404 B1 * | 1/2006 | Talton et al. | 424/490 |
| 7,001,672 B2 * | 2/2006 | Justin et al. | 428/615 |
| 7,063,748 B2 * | 6/2006 | Talton | 118/716 |
| 7,118,630 B1 * | 10/2006 | Balooch et al. | 118/726 |
| 7,169,317 B2 * | 1/2007 | Beaty | 216/109 |
| 7,666,522 B2 * | 2/2010 | Justin et al. | 428/615 |
| 7,985,367 B2 * | 7/2011 | Hiromatsu et al. | 264/400 |
| 2002/0098668 A1 | 7/2002 | Kim et al. | |
| 2003/0121887 A1 * | 7/2003 | Garvey et al. | 216/65 |
| 2003/0164371 A1 | 9/2003 | Bergsstrom et al. | |
| 2004/0033369 A1 | 2/2004 | Fleming et al. | |
| 2005/0061108 A1 | 3/2005 | El-Shall et al. | |
| 2005/0181141 A1 * | 8/2005 | Flanagan | 427/421.1 |
| 2005/0211680 A1 * | 9/2005 | Li et al. | 219/121.68 |

OTHER PUBLICATIONS

Caminat, P. et al., Double beam pulse laser deposition of NiMnSb thin films at ambient temperature. Thin solid films. Apr. 2004, vol. 453-454, Abstract.

Konov, V.I., "Pulsed laser deposition of hard coatings in atmospheric air", Appl. phys A., Sep.-Oct. 2004, vol. 79A, No. 4-6.

* cited by examiner

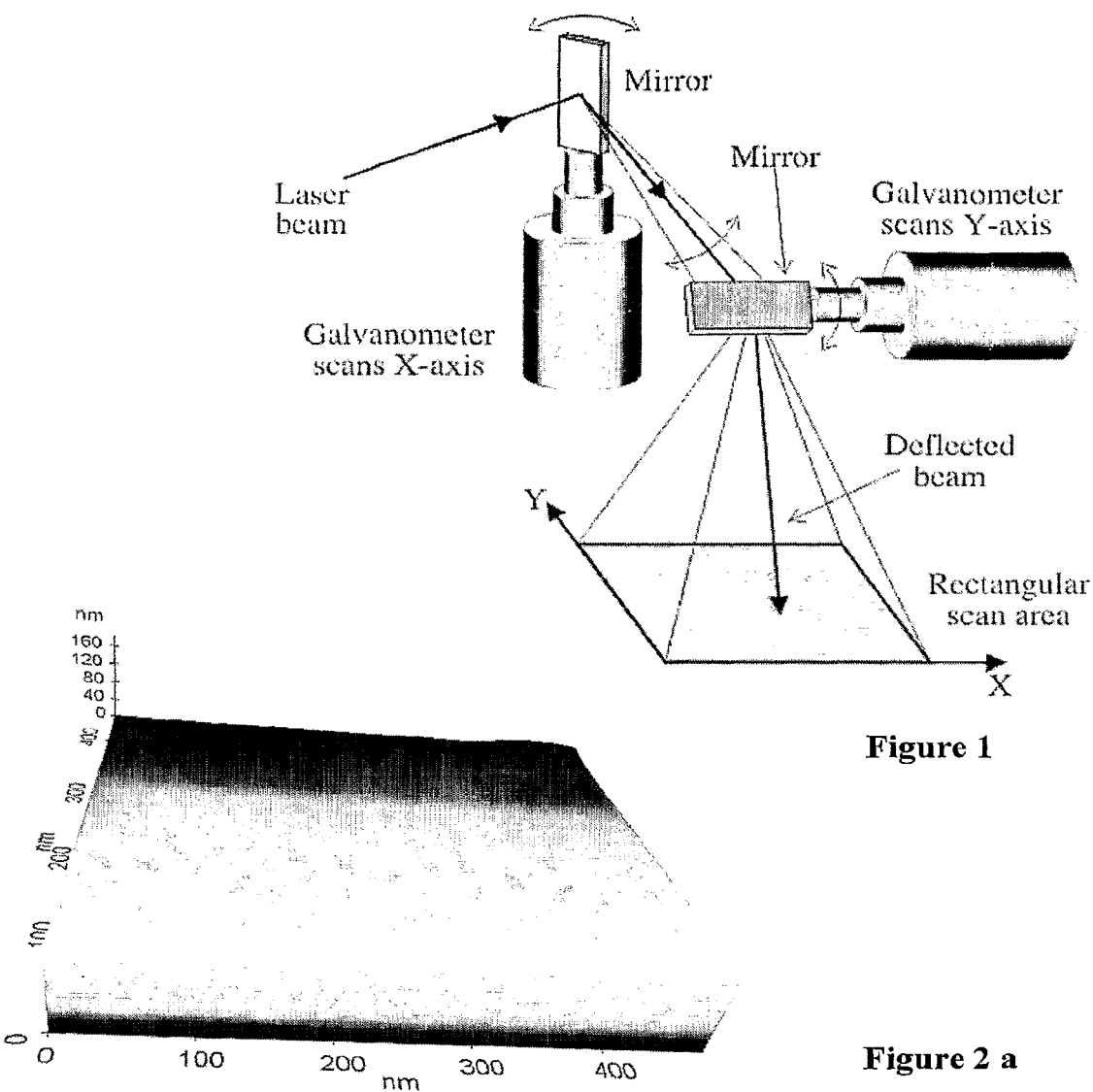
Figure 1
Figure 2 a
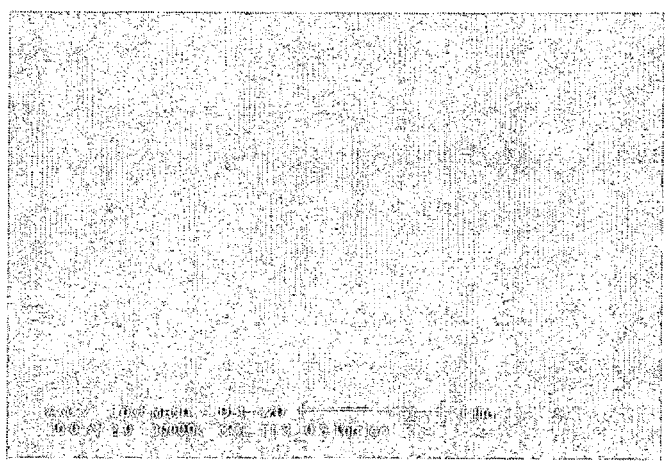
Figure 2b y = 50 -200 nm, for example 100 nm x = 1 µm - 1000 µm, for example 45 µm

COATING ON A MEDICAL SUBSTRATE AND A COATED MEDICAL PRODUCT

FIELD OF INVENTION

The invention relates generally to a method for coating surfaces of medical products, e.g. articulating surfaces of a joint or bone screws. The invention also relates to products coated by the method. The invention has many advantageous effects such as high coating production rate, excellent coating properties and low manufacturing costs.

BACKGROUND

Coating of Medical Products
Bone Screws

Several screw-dependent factors such as material of the screw, the screw diameter and length, the length of the threaded part, and the shape of the threads affect the forces experienced by the screws. Also the properties of the bone, such as the thickness of cortices and the density of bone, influence the forces required in screw installation and pullout. Screw failures during installation increase operation time and require the drilling of several holes in bone. Since drilling a hole into a bone reduces its torsional strength by 10-40% depending on the screw/bone diameter rate, it is essential to avoid screw failures during operations. Although current biomaterials are compatible for orthopaedic implants, various techniques are still used to enhance their properties. Different applications require specific properties even from the same material: in some cases implant is expected to stimulate bone ingrowth and increase attachment, but on the other hand inertness and low degradation rate may also be favourable in certain sections of the implant. Bone ingrowth and attachment can be enhanced by rough surfaces or textures on the implants. These surface conditions are achieved, for example, by different kinds of coating techniques or by etching. Smooth surfaces for preventing corrosion can be prepared by chemical or physical vapour deposition techniques. Amorphous diamond (AD) coatings can be produced by filtered pulsed arc discharge method which is one of the physical vapour deposition techniques. AD coating is reported to be even as hard as natural diamond, inert coating with low friction. Therefore, AD coatings should reduce the number of screw failures during installation as high torques leading to screw failures might be avoided. Also late removal of the screws is easier as less corrosion is expected.

Hip Implants

In total hip replacements, the bulk properties of materials, such as proper elasticity and hardness, are important. However, the material interacts with the body mainly at the surfaces. Wear and corrosion are initiated at the surfaces also. Therefore, the control of surface properties using different kinds of treatments or coatings may improve total hip replacements considerably. Until now, the surface treatments most studied included ion implantation and methods to control surface topography such as grit or sand blasting or plasma treatments. Among the large variety of coatings, hydroxyapatite, titanium oxide and nitride, zirconium oxide, pyrolytic carbon, and diamondlike carbon coatings have shown the most promising results. These coatings mainly are used to enhance bone growth; to minimize friction, wear, and corrosion; and to improve biocompatibility of total joint prostheses. The potential of novel coatings to solve some present problems in joint prostheses is discussed based on the structure and properties of different kind of coatings. It can be concluded that currently coating methods exist to improve the tribological performance and longevity of the total hip replacements. However, coatings must fulfill two essential requirements for successful long-term performance: no delamination in biochemical and biomechanical environments and sufficient protection of substrate from corrosion. These requirements have turned out to be an obstacle for development of reliable coating solutions for many medical applications.

Any implant material can be divided into two characteristic components: bulk material, which mainly is responsible for the mechanical and structural properties; and surface layer material, which interacts with the biologic environment. Throughout the history of total hip replacement (THR), the focus in material development has been the improvement of bulk properties of metals and, more recently, those of ceramics and polymers. For example, in the case of metals, minor improvements have been reached by alloying and novel processing techniques. Both of these approaches enhance the control of microstructure and composition, which are reflected in hardness and wear or corrosion resistance. For example, the yield strength of Co—Cr alloys have been improved from the typical values of cast alloys (450 MPa) to about 1350 MPa for high-temperature isostatic pressing alloys. Similar improvements have been achieved with Ti alloys and stainless steel, especially using mechanical deformation hardening. In the case of polyethylene (PE), the main achievement has been well-controlled cross-linking to enhance mechanical properties, especially wear resistance.

On the other hand, the properties of material surfaces have a major effect on interaction with tissues or components of modular prostheses. Novel techniques for surface treatment and deposition can be used to modify the surface of the implant, for example, to protect the implant from degradation and corrosion, to improve the surface structure or chemistry for tissue integration, or to increase wear resistance and to control friction at the interfaces. In most cases, these additional treatments can be used for existing clinically tested implant designs and bulk materials without adverse effects on component dimensions or bulk material properties.

Motivation for Coatings

Although bulk material properties have a major effect, for example, on elasticity or shock absorption properties of implants, properties of the surface layer are relevant for optimal behavior of each section of an implant. Low friction and wear rate are desirable at articulating surfaces and also at the other interfaces with micromotion between different components. Wear leads to release of debris particles to adjacent tissues, which can eventually cause aseptic loosening of an implant. Abrasive and adhesive wear are typical wear mechanisms. Abrasive wear (scratching) can be minimized using hard coatings or surface layers. Adhesive wear is related to sticking together of sliding surfaces, which can shear the softer material, in this case ultra-high molecular weight polyethylene (UHMWPE). In principle, adhesive wear could be minimized using materials with good wetting characteristics.

Different forms of corrosion in body fluids are a major concern especially in long-term clinical use. Modular THRs have several interfaces between different components, fixing materials, bone or synovial fluid for corrosion. Metallic elements used in orthopaedic implants are potential carcinogens or sensitizers of the immune system. However, either slight or no considerable risk for lymphoma or leukemia were found in patients who had a Co-alloy THR. On the other hand, the prevalence of metal sensitivity among patients with implant failure is approximately five times higher than the incidence in the normal population and two to three times higher than that of all patients with metal implants. Fortunately, different corrosion mechanisms could be avoided or at least diminished by biocompatible, high-quality, corrosion-resistant coatings. Although Ti alloys generally are considered to be nontoxic, they can be severely corroded because of crevice corrosion in an acidic environment, for example, at the stem-bone cement interface. Therefore, Ti alloys should be surface modified if used in contact with the bone cement or on articulating surfaces. As mentioned above, coatings can protect the implant against bone-cement fixation. In the case of press-fit acetabular cups and stems, in which the long-term fixation is based on bone ingrowth, implant surfaces can be manufactured to adapt better to bone using several methods such as meshing, texturing, and porous or bioactive coatings. Depending on the design strategy, these coatings either should be dissolved gradually or should provide a stable, nondissolving interface for bone growth. The properties of all the implant surfaces could be improved using coatings or surface treatments; however, this is not always necessary or commercially realistic.

Methods for Surface Modification

The idea of surface modification is to retain the desired bulk properties while modifying only the outermost surface, which interacts with the surrounding tissues and fluids or other components of the implants. Surface-modification methods, can be divided into two categories: (1) chemical, physical, or biologic modification of existing surface or surface layer; and (2) covering the bulk material with a material having different composition or microstructure. In principle, only the outermost molecular layers, that is the depth of about 1 nm, need to be modified or deposited. However, extremely thin layers easily are eroded or worn out, and therefore, the practical modified zone should be thicker, a few hundred nanometers or even several micrometers. This thickness can be compared with a typical dissolution rate of metallic implant materials in the body, about 50 nm/year.

Some typical methods used for surface modification of orthopaedic implants are summarized in the following. Because in most of the cases, the treatment or deposition process occurs at an atomic level, it is crucial to clean the implant surface before treatment using mechanical, chemical, plasma, or ion-beam methods. These methods remove contamination such as water vapor and hydrocarbons from the surface. In the physical vapor deposition (PVD) processes, deposition is carried out in vacuum and in most cases, energetic atoms, ions, or plasma (ionized gas) are used. Energetic ions make it possible to reach high local temperatures on ion impact or on the growing surface layer. Generally, this is advantageous because samples can be kept at low temperatures during treatment and still the films grow dense with a fine microstructure, leading to improved mechanical properties and corrosion resistance. Ion implantation is one of the best controlled PVD processes, in which accelerated ions with energies in the range of 10 to $10^6$ eV are used to bombard the surface. With these energies, the range of ions varies from a few atomic layers to a few hundred nanometers. Ions can be formed from most of the atoms in the periodic table, and the energy and dose (total number of ions per unit area) can be determined accurately. Therefore, ion implantation has been used frequently for fundamental studies of the effects of dopant (added impurity) ions and for commercial applications in the electronics industry and also in biomedical companies such as Spire Corporation (Bedford, Mass.) and Implant Sciences Corporation (Wakefield, Mass.). Although ion beams often are used to improve corrosion or wear resistance, they can be used to modify polymer surfaces, too. Ion beams or plasma ion treatments can form, for example, nitrogen or oxygen functionalities, on the surface. These change important characteristics such as a hydrophobic polymer to a hydrophilic one, which enhances biocompatibility and wettability in biologic fluids. In a similar manner, hydrophobic properties can be achieved using higher-degree fluorinated compounds as a source for plasma ions.

Sputtering is one of the mostly used commercial processes to produce adherent films of metals, oxides, carbides and nitrides, even on large surfaces, at affordable prices. By proper selection of process parameters (gas pressure and composition, discharge, and bias voltage) thick, dense, fine-grained films can be deposited, which even can survive without delamination in corrosive body fluids and can withstand high surface pressures. Different variants of plasma techniques (dc, rf or laser plasma, plasma implantation, plasma etching, plasma arc, or pulsed plasma arc) are used to clean and etch the surfaces, to modify cell and protein reactions, to implant ions, to deposit coatings, and others. In fact plasma-surface modification is an effective and economical technique for many biomaterials and is of growing interest in biomedical engineering because of several advantages: reliability, reproducibility, nonline-of sight, sterile technique, relatively inexpensive, compatible with masking techniques to enable surface patterning, large selection of varied surface parameters, and others. Surface analysis is needed to ensure that the intended surface structures, compositions and properties really are achieved. Plasma-deposited films usually are almost free of voids and pinholes and show good adhesion to the substrate, which are remarkable advantages.

Chemical vapor deposition is based on the dissociation of gas molecules in a flow gas reactor to leave the desired atoms at the sample surface. Typically, high temperatures are needed and the coatings consist of large grains, which leave open corrosion paths for ions to the substrate. Because of these difficulties, chemical vapor deposition methods generally are not applied for orthopaedic applications. Microstructure of a coating is one of the most important parameters affecting the outcome of the coating in a biologic environment. The structure quite often is related to many functional properties of coatings such as hardness or corrosion resistance. In principle, the most perfect microstructure would be a single crystalline film, which is a fully dense, uniform structure where atoms or molecules are located in a perfect periodic structure. This kind of a structure is strong and can protect the substrate against corrosion, if the coating material is not dissolved at an atomic level. However, perfect single crystals cannot be grown on common implant materials. The next best solution is an amorphous structure such as amorphous diamond. This structure is less dense than a single crystal, but generally is uniform and smooth without open corrosion paths such as grain boundaries. Polycrystalline films, especially if they have oriented structures such as columnar grains, offer poor resistance against corrosion unless a corrosion resistant intermediate film is used between the substrate and the coating.

Delamination resistance of any orthopaedic coating is very important. High adhesion and delamination resistance can be achieved in different ways in deposition methods, for example, by covalent bonding between the substrate and the coating or surface layer, by intermixing layers or graded structures at the interface, appropriate functional groups for strong intermolecular adhesion etc.

The wear of PE in implants can be divided roughly into two components: adhesive and abrasive wear. Adhesive wear is characterized by the sticking of the polymer surface to a countersurface, leading to shearing of polymer material. This process produces micrometer-sized wear particles. In principle, wear is minimized by using wettable surfaces (higher surface energy, a water drop spreads easily). The wetting properties of surfaces and coatings such as amorphous diamond also can be tailored in a wide range using added impurities, for example, metals, F, K, P, and Ca. Abrasive wear (scratching) is caused by the surface roughness of the counterpart material and can be increased considerably by third-body abrasive particles or components of the lubricating fluid. With respect to both of these wear mechanisms, metals and ceramics behave fundamentally differently, especially in long-term clinical use. The ceramic oxides (alumina, zirconia) are more wettable than the metal surfaces, although a passivating oxide or oxyhydroxide film is formed on the surface of Co—Cr alloys, stainless steels, and Ti alloys. These passivating films are approximately 2 nm to 5 nm thick and are damaged easily by third-body wear particles or are sheared off. These third-body particles may derive from bone debris; polymethylmethacrylate; or oxide, carbide, or nitride particles from metal surfaces. The cyclic wear process, because of repeated shearing off and reforming of passivating film, generally is called oxidative wear. Although the typical average surface roughness of metal femoral heads initially is in the range 0.01 to 0.05 µm, the roughness of articulating metal surfaces increases with time because of the aforementioned reasons.

Ceramics and ceramic coatings are harder than normal third body particles in synovial fluid, such as, bone or bone cement. Therefore, they should remain smooth in long-term clinical use and the wear rate of possible soft counterpart material (UHMWPE) should not increase because of surface roughening. Indeed, based on the simulator experiments and clinical trials, ceramic surfaces remain stable and minimize long-term PE wear with typically 2 times to 4 times lower wear than with Co—Cr—Mo heads. In hard sliding pairs, ceramic-on-ceramic articulations are an enticing choice because of good wear resistance. In this combination, in addition to smoothness, an accurate fit of articulating surfaces is even more important than with pairs using PE. Current manufacturing techniques provide tolerances of surface sphericity better than 1 µm. These well-matched ball-cup pairs should allow hydrodynamic lubrication with a continuous fluid film. However, the clinical surveys have showed that articulating surfaces partly are in contact and that adhesive and abrasive wear occur. Therefore, in the case of identical sliding pairs, the materials should be as hard as possible to minimize wear. Even in this case, ceramic coatings could offer several advantages. For example, because of extreme hardness and good tribologic characteristics of diamond, continuous film lubrication is not needed in the case of amorphous diamond coatings. When the coating is thick enough (>20 microns), it can withstand high contact stresses and wear rate is negligible (less than 10 nm per 15 million cycles in a simulator). Furthermore, coefficient of friction is fairly low (<0.1) even in the early stages of an implant life cycle. Low friction is accompanied by low bending torque on fixation surfaces of the prostheses. The most important advantage of ceramic coatings compared with bulk ceramics, perhaps, is the fact that they are less prone to sudden complete failure, which is a feared, rare (less than 0.1%) complication of current ceramic-on-ceramic total hip sliding pairs.

In addition to articulating surfaces, wear occurs on all interfaces moving with respect to each other. For example, because of different elasticity of materials under cyclic loading, it seems impossible to achieve permanent rigid fixation of a stem using bone cement. Most of the stem designs allow movement (subsidence, micromotion) at the interface between bone cement and stem. However, the bone cement-bone interface is meant to be stable. Bone cements contain hard particles of $ZrO_2$ or $BaSO_4$, which are two agents commonly used to make bone cement radiopaque. These ceramic particles easily scratch any metal surface. However, hard ceramic coatings provide superior wear and corrosion resistance on the stem or cup surface against bone cement.

Protection Against Corrosion

In order to achieve good long-term clinical outcomes, the coatings must fulfill two essential requirements: they must be thick enough to withstand the high contact stresses against third-body particles and they must avoid delamination, which can be caused by corrosion through the pinholes of the coating. The process is stimulated when a surface layer contains micrometer-sized defects and especially if it is cathodic relative to its substrate Because of these reasons, poor long-term clinical results have been obtained, e.g. with TiN and oxide coatings. Surface roughness increases rapidly because of partial delamination of the coating, and the rough surface increases the wear rate of soft PE counterpart material.

In principle, surface treatments such as ion implantation, nitriding, or oxidation modifying the surface layer can be used to improve the hardness and corrosion resistance of metals and to reduce PE wear. In short-term laboratory tests, considerable improvements have been made because of the increase of surface hardness of metal. However, in long-term tests and in clinical use, the modified surface layer gradually becomes damaged by corrosion and hard third-body particles. For example, in the case of nitrogen-implanted Ti-6Al-4V total knee femoral components, the wear rate and roughness of bearing surfaces increased significantly ($R_a$ even 1-2 µm) after only 1 to 3 million wear cycles, which is the same level as in the unimplanted case. In the case of similar Co—Cr alloy components, the surface removal rate was approximately 0.06 to 0.10 µm per 1 million cycles, and the possible advantageous effects of implantation, unfortunately, are assumed to be lost on articulating surfaces within a few years in vivo. Conversely, relatively thick, pin-hole-free ceramic coatings could be used on metal implants to provide inherent stability, to avoid long-term surface roughening, and to reduce wear of PE or cartilage. However, only a few successful results using the coatings for articulating surfaces have been published. Based on the reduction of polyethylene wear with zirconium oxide, titanium nitride or amorphous diamond coating on the counterface material even by 10 times to 50 times compared with uncoated Co—Cr femoral heads in laboratory tests, these coatings have great potential as a lifetime bearing combination.

One of the major problems in the use of hip and knee implants is the huge selection of different types of prostheses with a wide range of properties such as surface roughness, tolerances, and microstructural aspects leading to similar scatter in survival statistics. However, the well-functioning prostheses degrade, too. For example, Jacobs et al found that 3 years postoperatively, concentrations of implant metals in the serum and urine increased three-fold to eight-fold.

Functionalizing the Surface

In most of the applications discussed above, the role of the coating is quite passive from a biologic point of view, that is, it does not actively interact and enhance tissue function. However, low-temperature deposition processes such as surface-induced mineralization or sol-gel deposition can be used to attach proper functional groups on the surface in a series of self-assembled monolayers. Then, for example, a calcium phosphate coating can be grown from a liquid phase even on porous surfaces to get a rather uniform coverage. Growth factors to accelerate bone growth simply can be co-deposited with the coating at physiologic conditions.

Osseous integration effectively can be enhanced by polymer coatings such as poly d,l-lactide on pins or screws. Polymer coatings also can be deposited using simple methods such as dipping, and proper complexes of pharmaceutical agents such as growth factors can be incorporated in the polymer matrix. The polymer matrix and the amount of agents can be used to control the degree of aqueous diffusion into and out of the coating and drug solubility. Implant surfaces also can be covered by living cells, for example, by feeding sugar molecules for cells to cover their surface, which then can be used to attach cells on the implant surface and thus improve cell growth on the surface.

Ion, plasma and laser beams, and atomic-level mixing on the surface have been used conventionally to improve wear and corrosion of implant materials. However, they also can be used effectively to incorporate high amounts of calcium, phosphate, bioactive ceramics, or other species to reduce bone resorption and improve bone and implant integration. These techniques, in addition to photolithography, can be used to produce well-defined microstructural surfaces to promote cell attachment.

Laser-Ablation

In the recent years, considerable development of the laser technology has provided means to produce very high-efficiency laser systems that are based on semi-conductor fibres, thus supporting advance in so called cold ablation methods.

At the priority date of the current application, solely fibrous diode-pumped semiconductor laser is competing with light-bulb pumped one, which both have the feature according to which the laser beam is lead first into a fibre, and then forwarded to the working target. These fibrous laser systems are the only ones to be applied in to the laser ablation applications in an industrial scale. The recent fibres of the fibre lasers, as well as the consequent low radiation power seem to limit the materials to be used in the vaporization/ablation as the vaporization/ablation targets. Vaporizing/ablating aluminium can be facilitated by a small-pulsed power, whereas the more difficult substances to be vaporized/ablated as Copper, Tungsten, etc. need more pulsed power. The same applies into situation in which new compounds were in the interest to be brought up with the same conventional techniques. Examples to be mentioned are for instance manufacturing diamond directly from carbon (graphite) or alumina production straight from aluminium and oxygen via the appropriate reaction in the vapour-phase in post-laser-ablation conditions. When employing novel cold-ablation, both qualitative and production rate related problems associated with coating exist, thin film production as well as cutting/grooving/carving etc. has been approached by focusing on increasing laser power and reducing the spot size of the laser beam on the target. However, most of the power increase was consumed to noise.

SUMMARY OF THE INVENTION

Neither recent high-technological coating methods) nor present coating techniques related to laser ablation either in nanosecond or cold ablation range (pico-, femto-second lasers) can provide any feasible method for industrial scale coating of articulating surfaces of medical products.

The present CVD- and PVD-coating technologies require high-vacuum conditions making the coating process batch wise, thus non-feasible for industrial scale coating of most of the present metal products. Moreover, the distance between the metal material to be coated and the coating material to be ablated is longs typically over 50 cm, making the coating chambers large and vacuum pumping periods time- and energy-consuming. Such high-volume vacuumed chambers are also easily contaminated with coating materials in the coating process itself requiring continuous and time-consuming cleaning processes. All this makes the coating of articulating surfaces with present method very slow, and thus increase heavily the price of the products making them unavailable for most of the mankind.

While trying to increase the coating production rate in present laser-assisted coating methods, various defects such as pinholes, increased surface roughness, decreased or disappearing optical properties, particulates on coating surface, particulates in surface structure affecting corrosion pathways, decreased surface uniformity, decreased adhesion, unsatisfactory surface thickness and tribological properties etc. take place.

A first object of this invention is to provide a new method how to solve a problem to coat for example articulating surfaces of a medical product with pulsed laser ablation. Thus, the method can be applied for coating both the articulating surface of the medical product or whole or part of the remaining medical product.

A second object of this invention is to provide new medical products of which the articulating surface has been coated by pulsed laser deposition.

A third object of this invention is to provide at least a new method and/or related means to solve a problem how to provide available such fine plasma practically from any target to be used in coating of surfaces of medical products, so that the target material do not form into the plasma any particulate fragments either at all, i.e. the plasma is pure plasma, or the fragments, if exist, are rare and at least smaller in size than the ablation depth to which the plasma is generated by ablation from said target.

A fourth object of the invention is to provide at least a new method and/or related means to solve how to coat the surface area of a medical product with the fine plasma without particulate fragments larger in size than the ablation depth to which the plasma is generated by ablation from said target, i.e. to coat substrates with pure plasma originating from practically any material.

A fifth object of this invention is to is to provide a good adhesion of the coating to the surface of a medical product by said pure plasma, so that wasting the kinetic energy to particulate fragments is suppressed by limiting the existence of the particulate fragments or their size smaller than said ablation depth. Simultaneously, the particulate fragments because of their lacking existence in significant manner, they do not form cool surfaces that could influence on the homogeneity of the plasma plume via nucleation and condensation related phenomena.

A sixth object of the invention is to provide at least a new method and/or related means to solve a problem how to provide a broad scanning width simultaneously with fine plasma quality and broad coating width even for larger articulating surfaces of medical products in industrial manner.

A seventh object of the invention is to provide at least a new method and/or related means to solve a problem how to provide a high repetition rate to be used to provide industrial scale applications in accordance with the objects of the invention mentioned above.

An eighth object of the invention is to provide at least a new method and/or related means to solve a problem how to provide fine plasma for coating of surfaces of medical product to manufacture products according to the first to seven objects, but still save target material to be used in the coating phases producing same quality coatings/thin films where needed.

A further object of the invention is to use such method and means according previous objects to solve a problem how to cold-work and/or coat surfaces for coated products.

The present invention is based on the surprising discovery that surfaces of medical products like articulating surfaces can be coated with industrial production rates and excellent qualities regarding one or more of technical features such as chemical and/or wear resistance, scratch-free-properties, thermal resistance, coating adhesion, tribological properties, particulate-free coatings, pinhole-free coatings and biocompatibility by employing ultra short pulsed laser deposition in a manner wherein the laser pulse is scanned with pulse repetition rate of at least 1 Mhz. Preferably, the coating is conducted in a manner wherein pulsed laser beam is scanned with a rotating optical scanner comprising at least one mirror for reflecting said laser beam.

Moreover, the present method accomplishes the economical use of target materials, because they are ablated in a manner accomplishing the reuse of already subjected material with retained high coating results. The present invention further accomplishes the coating of articulating surfaces of medical products in low vacuum conditions with simultaneously high coating properties. Moreover, the required coating chamber volumes are dramatically smaller than in competing methods. Such features decrease dramatically the overall equipment cost and increase the coating production rate. In many preferable cases, the coating equipment can be fitted into production-line in online manner.

The coating deposition rates with 20 W USPLD-apparatus are 2 mm³/min. While increasing the laser power to 80 W, the USPLD coating deposition rate is increased to 8 mm³/min, accordingly. According to the invention, the increase in deposition rate can now be fully employed to high quality coating production.

In this patent application the term "coating" means forming material of any thickness on a substrate. Coating can thus also mean producing thin films with thickness of e.g. <1 μm.

The structure of the coatings depends on the selected deposition parameters, e.g. amorphous diamond, nano-crystalline diamond or pseudo-monocrystalline diamond as well as other carbon based coatings comprising also nitrogen and/or boron can be realized with the these techniques.

Various embodiments of the inventions are combinable in suitable part.

When read and understood the invention, the skilled men in the art may know many ways to modify the shown embodiments of the invention, however, without leaving the scope of the invention, which is not limited only to the shown embodiments which are shown as examples of the embodiments of the invention.

FIGURES

Figure 6:
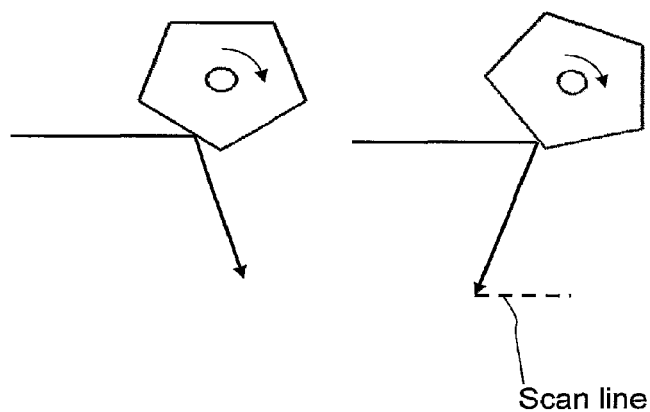
Figure 7:
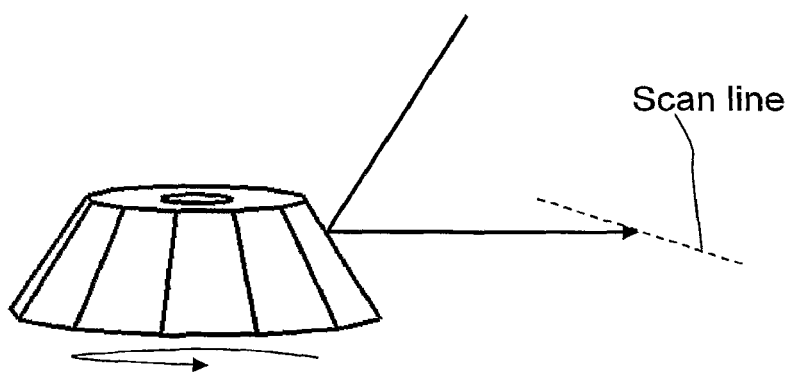
Figure 8:
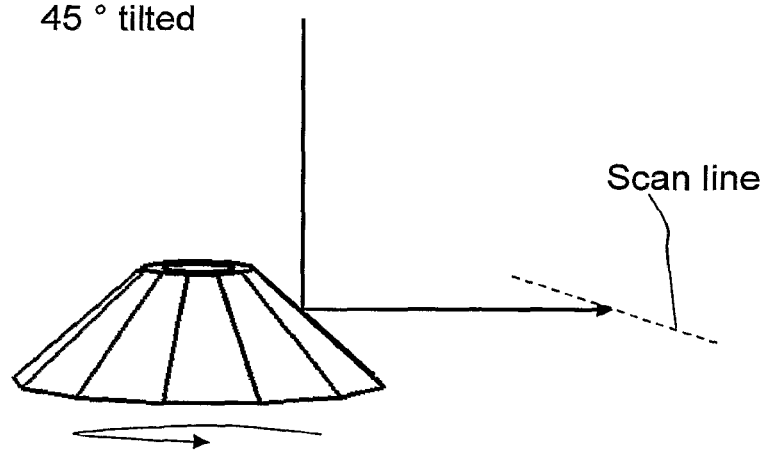
Figure 9A:
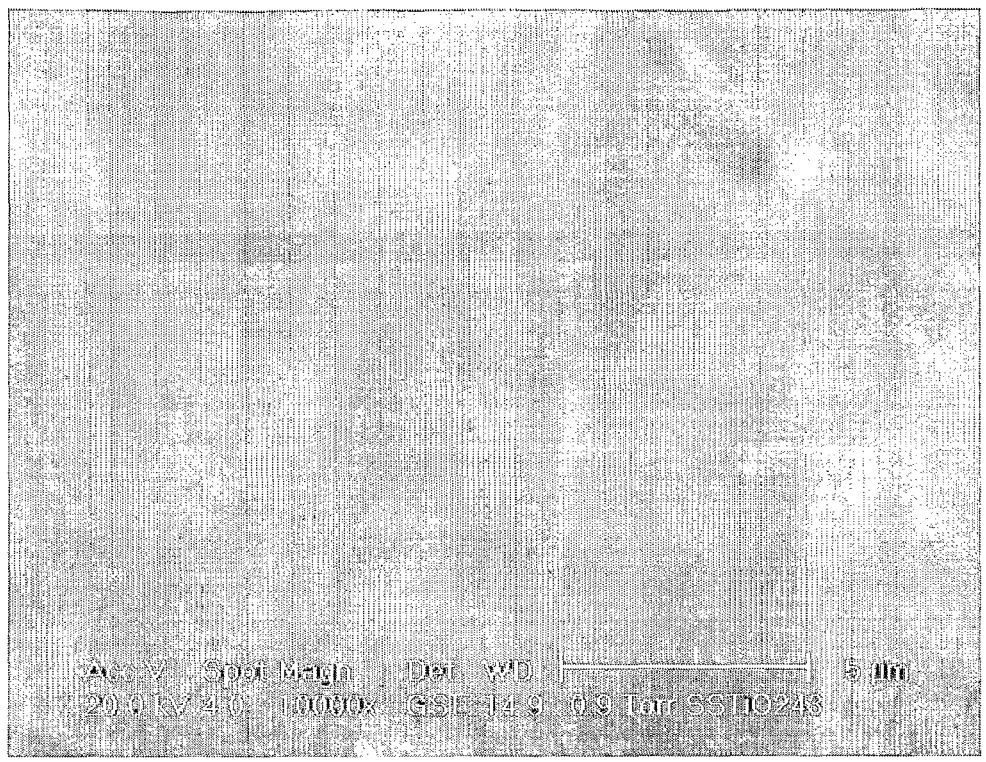
Figure 9B:
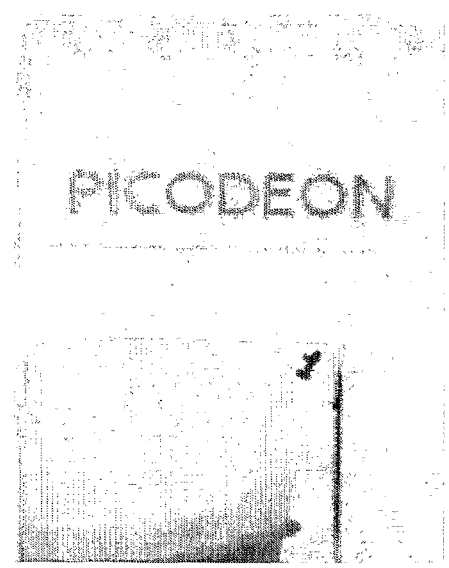

The described and other advantages of the invention will become apparent from the following detailed description and by referring to the drawings where:

FIG. 1. illustrates an exemplary galvano-scanner set-up comprising two galvano-scanners employed in state of the art cold ablation coating/thin-film production and in machining and other work-related applications. The number of galvano-scanners directing the laser beam varies but is typically limited to one single galvano-scanner, FIG. 2a. illustrates AFM image of one AD coating on Si according to the invention on Si on the left, FIG. 2b. illustrates ESEM picture AFM image of one AD coating on Si according to the invention, FIG. 3. illustrates the situation wherein prior art galvanometric scanner is employed in scanning laser beam resulting in heavy overlapping of pulses with repetition rate of 2 Mhz, FIG. 4. illustrates one possible turbine scanner mirror employed in method according to the invention, FIG. 5. illustrates the movement of the ablating beam achieved by each mirror in the example of FIG. 4, FIG. 6. illustrates beam guidance through one possible rotating scanner to be employed according to the invention, FIG. 7. illustrates beam guidance through one possible rotating scanner to be employed according to the invention, FIG. 8. illustrates beam guidance through one possible rotating scanner to be employed according to the invention, FIG. 9a. illustrates one $TiO_2$ coating according to the invention deposited from Ti target on steel and glass showing high optical quality and smoothness FIG. 9b. illustrates ESEM-picture of FIG. 9a, FIG. 10. illustrates plasma plume directions according to the invention in the deposition of coating on a bone screw. The screw is rotated around its symmetry axis during deposition, FIG. 11. illustrates deposition of coatings according to the invention at different angles to reach optimal deposition for a hip joint ball. The ball is rotated around its symmetry axis during deposition, FIG. 12. illustrates deposition of coatings according to invention at different angles to reach optimal deposition for a hip joint cup. The cup is rotated around its symmetry axis during deposition, FIG. 13a. illustrates an embodiment according to the invention, wherein target material ablated by scanning the laser beam with rotating scanner (turbine scanner).

Figure 13A:
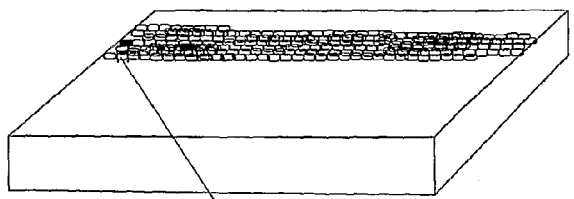
Figure 13B:
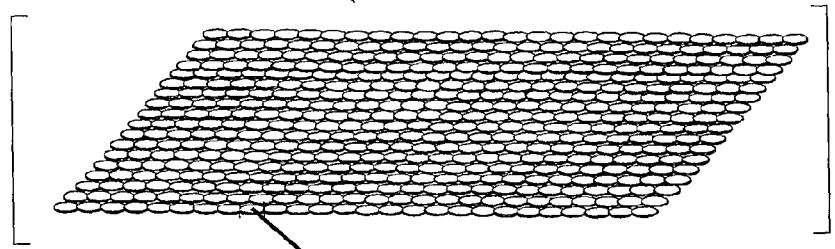

FIG. 13b. illustrates an exemplary part of target material of FIG. 13a.

Figure 13C:
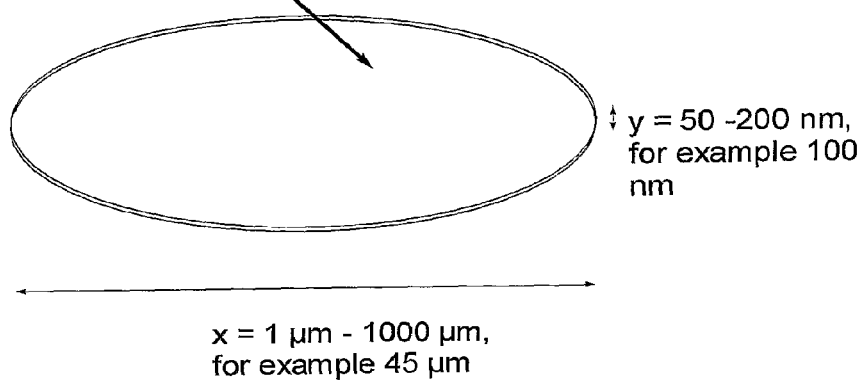

FIG. 13c. illustrates an exemplary ablated area of target material of FIG. 13b.

Figure 14:
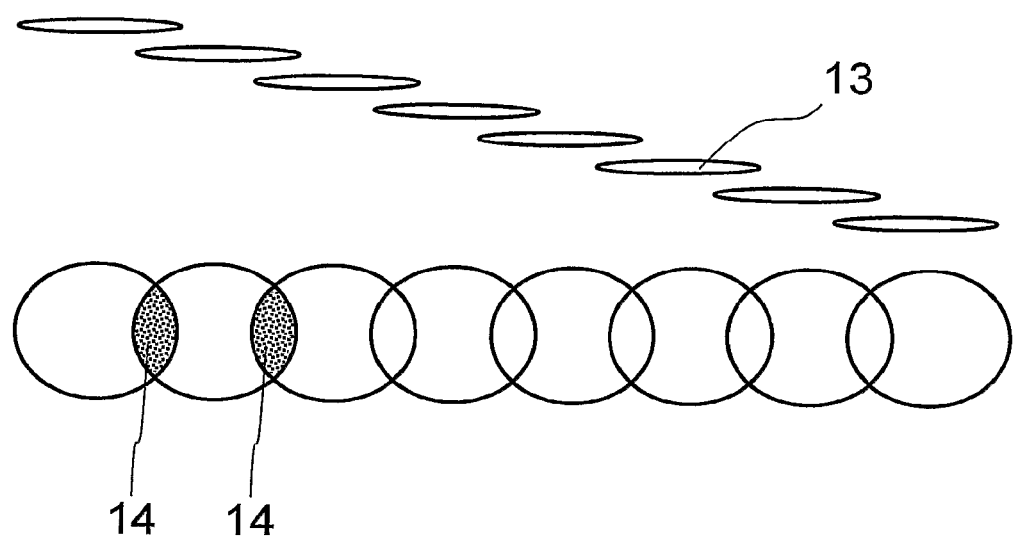

FIG. 14 illustrates an exemplary way according to the invention to scan and ablate target material with turbine scanner (rotating scanner).

Figure 15A:
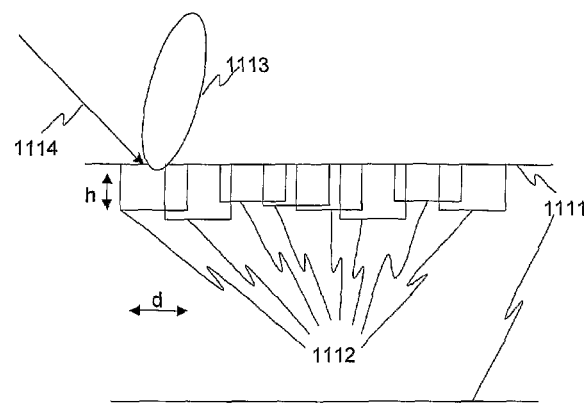
Figure 15B:
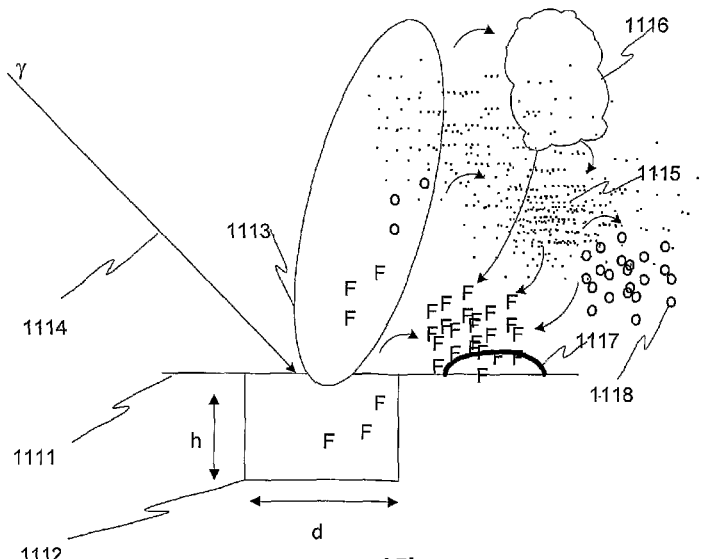

FIG. 15a and FIG. 15b demonstrate plasma related quality problems, which indicate plasma generation according to known techniques.

FIG. 16a and FIG. 16b demonstrate plasma related quality problems, which indicate plasma generation according to known techniques.

DETAILED DESCRIPTION OF EMBODIMENTS OF THE INVENTION

According to the invention there is provided a method for coating a surface of a medical product like articulating surface in which method the coating is carried out by employing ultra short pulsed laser deposition comprising a pulse frequency of at least 1 MHz.

In industrial applications, it is important to achieve high efficiency of laser treatment. In cold ablation, the intensity of laser pulses must exceed a predetermined threshold value in order to facilitate the cold ablation phenomenon. This threshold value depends on the target material. In order to achieve high treatment efficiency and thus, industrial productivity, the repetition rate of the pulses should be high, such as 1 MHz, preferably over 2 MHz and more preferably over 5 MHz. The requirement increases once the surface area to be treated increases and/or coating thickness increases.

In one embodiment of the invention, said surface of the medical product is coated with metal, metal oxide, metal nitride, metal carbide or mixtures of these. Especially advantageous metals include titanium, tantalum, vanadium, chromium, cobalt and molybdenum.

In another embodiment of the invention, said articulating surface of the medical product is coated with carbon material comprising over 90 atomic-% of carbon, with more than 70% of sp3-bonding. Such advantageous materials include but are not limited to amorphous diamond, nano-crystalline diamond or pseudo-monocrystalline diamond.

In a still another embodiment of the invention, said articulating surface of the medical product is coated with material comprising carbon, nitrogen and/or boron in different ratios. Such advantageous materials include but are not limited to boron carbon nitride, carbon nitride, boron nitride, boron carbide or thin films of boron carbon nitride or phases of different hybridizations of B—N, B—C and C—N phases. According to one embodiment of the invention, said articulating surface of the medical product can also be coated with a multilayered coating.

In one preferred embodiment of the invention, the coating is produced in a manner wherein coating thickness is at least 1 μm. In a second, more preferably embodiment of the invention the coating thickness is between 10 μm to 20 μm. In not specially abrasive conditions, the coating thickness can even be lower than 1 μm. The coating thicknesses must not be limited to those, because the present invention accomplishes the preparation of molecular scale coatings on the other hand, very thick coatings such as 100 μm and over, on the other hand.

In a preferred embodiment of the invention, the surface of the medical product is produced in manner that the produced coating contains less than one pinhole per 1 $mm^2$, preferably less than one pinhole per 1 $cm^2$ and most preferably no pinholes at the surface of the medical product. This is especially important on critical surfaces of an implant such as articulating or fixation surfaces. The coating can be arrange in a manner wherein only the articulating surface is coated.

In another preferred embodiment of the invention, the articulating surface of the medical product is produced in a manner wherein the first 50% of the produced articulating surface layer does not contain any particles having a diameter exceeding 1000 nm, preferably 100 nm and most preferably 30 nm.

If the early stages of the coating manufacturing process produces micrometer sized particles, such particles can cause open corrosion pathways in the next layers of the produced coating. Moreover, due to possibly and most probably irregular shape of the particles, it is extremely difficult to seal the surface underneath such particles. Additionally, such particles increase surface roughness substantially.

In another preferred embodiment of the invention the articulating surface of the medical product is coated in a manner wherein the average surface roughness of produced articulating surface layer is less than 100 nm as scanned from an area of 1 $μm^2$ with Atomic Force Microscope (AFM).

In another preferred embodiment of the invention the articulating surface of the medical product is coated in a manner wherein the pulsed laser beam is scanned with a rotating optical scanner comprising at least one mirror for reflecting said laser beam.

Ultra Short Laser Pulsed Deposition is often shortened USPLD. Said deposition is also called cold ablation, in which one of the characteristic features is that opposite for example to competing nanosecond lasers practically no heat transfer takes place from the exposed target area to the surroundings of this area, the laser pulse energies being still enough to exceed ablation threshold of target material. The pulse lengths are typically under 50 ps, such as 5-30 ps. i.e. ultra short, the cold ablation being reached with pico-second, femto-second and atto-second pulsed lasers. The material evaporated from the target by laser ablation is deposited onto a substrate that is held near room temperature. Still, the plasma temperature reaches 1,000,000 K on exposed target area. The plasma speed is superior, even gaining 100,000 m/s and thus, better prospective for adequate adhesion of coating/thin-film produced.

As mentioned earlier, it is advantageous not to direct several pulses into same location of the target surface because this causes a cumulating effect in the target material, with particle deposition leading to bad quality plasma and thus, bad quality coatings and thin-films, undesirable eroding of the target material, possible target material heating etc. Therefore, to achieve a high efficiency of treatment, it is also necessary to have a high scanning speed of the laser beam. According to the invention, the velocity of the beam at the surface of the target should generally be more than 10 m/s to achieve efficient processing, and preferably more than 50 m/s and more preferably more than 100 m/s, even such speeds as 2000 m/s. However, in the optical scanners based on vibrating mirror the moment of inertia prevents achieving sufficiently high angular velocity of the mirror. The obtained laser beam at the target surface is therefore just a few m/s, FIG. 1 illustrating an example of such vibrating mirror, also called galvano-scanner. The irregular speed of the scanner is transferred into coating procedure by irregular ablation of the target material, the target material being more heavily used in the ends of the scanned target area. This in turn results in irregular plasma quality and volume in the various parts of the plasma plume and thus, easily to irregular formation of coatings. The problem can be somewhat eased by employing only part of the plasma plume into coating. According to one embodiment of the invention, such an approach can is used to coat medical items comprising small articulating surfaces.

As the present coating methods employing galvano-scanners can produce scanning widths at most 10 cm, preferably less, the present invention also accomplishes much broader scanning widths such as 30 cm and even over 1 meter with simultaneously excellent coating properties and production rates.

Figure 4:
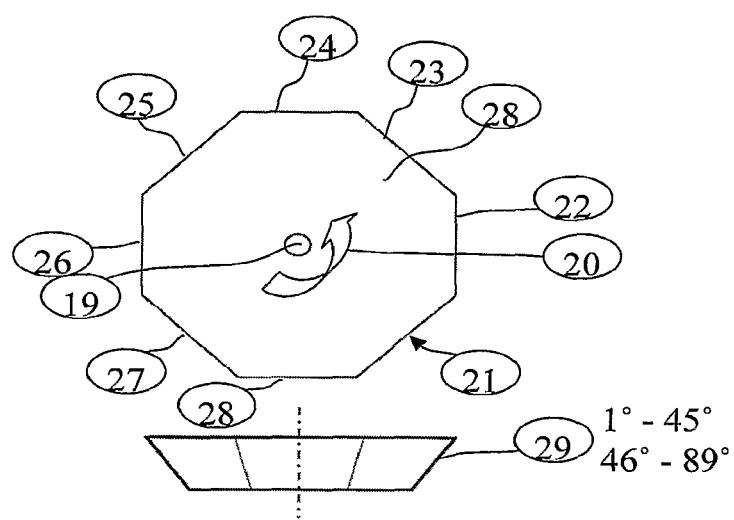

According to one embodiment of the invention, rotating optical scanner is here meant scanners comprising at least one mirror for reflecting laser beam. Such a scanner and its applications are described in patent application FI20065867. According to another embodiment of the invention, rotating optical scanner comprises at least three mirrors for reflecting laser beam. In one embodiment of the invention, in the coating method employs a polygonal prism illustrated in FIG. 4. Here, a polygonal prism has faces 21, 22, 23, 24, 25, 26, 27 and 28. Arrow 20 indicates that the prism can be rotated around its axis 19, which is the symmetry axis of the prism. When the faces of the prism of the FIG. 4 are mirror faces, advantageously oblique in order to achieve scanning line, arranged such that each face in its turn will change, by means of reflection, the direction of radiation incident on the mirror surface as the prism is rotated around its axis, the prism is applicable in the method according to an embodiment of the invention, in its radiation transmission line, as part of a rotating scanner, i.e. turbine scanner. FIG. 4 shows 8 faces, but there may be considerably more faces than that, even dozens or hundreds of them. FIG. 4 also shows that the mirrors are at the same oblique angle to the axis, but especially in an embodiment including several mirrors, the said angle may vary in steps so that, by means of stepping within a certain range, a certain stepped shift on the work spot is achieved on the target, illustrated in FIG. 5, among other things. The different embodiments of invention are not to be limited into various turbine scanner mirror arrangements regarding for example the size, shape and number of laser beam reflecting mirrors.

Figure 5:
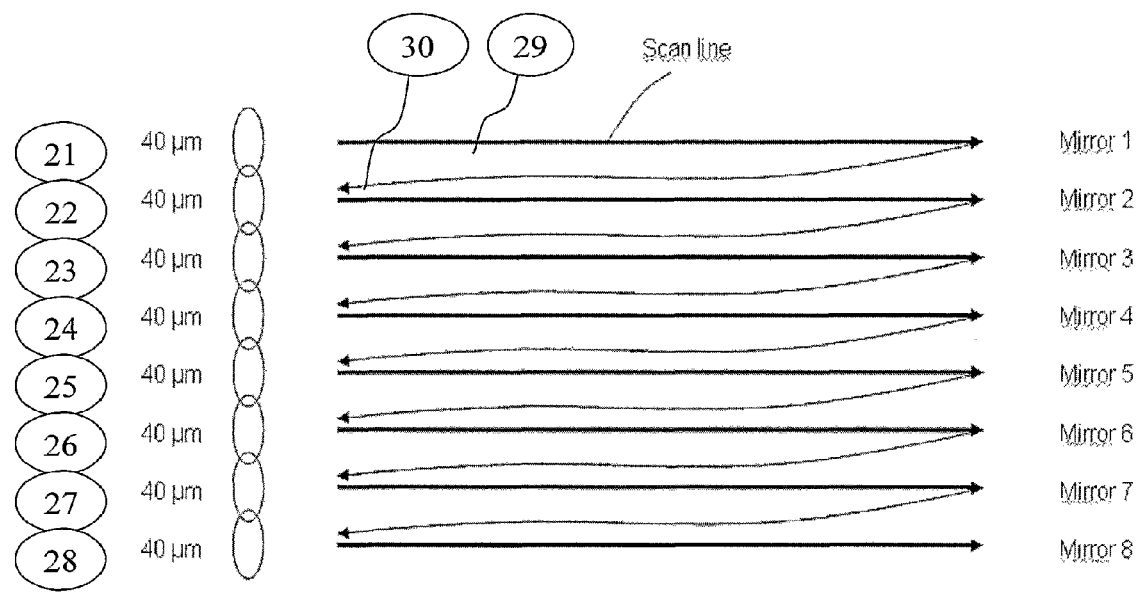

The structure of the turbine scanner, FIG. 4, includes at least 2 mirrors, preferably more than 6 mirrors, e.g. 8 mirrors (21 to 28) positioned symmetrically around the central axis 19. As the prism 21 in the turbine scanner rotates 20 around the central axis 19, the mirrors direct the radiation, a laser beam, for instance, reflected from spot 29, accurately onto the line-shaped area, always starting from one and the same direction (FIG. 5). The mirror structure of the turbine scanner may be non-tilted (FIG. 6) or tilted at a desired angle, e.g. FIGS. 7 and 8. The size and proportions of the turbine scanner can be freely chosen. In one advantageous embodiment of the coating method it has a perimeter of 30 cm, diameter of 12 cm, and a height of 5 cm.

In an embodiment of the invention it is advantageous that the mirrors 21 to 28 of the turbine scanner are preferably positioned at oblique angles to the central axis 19, because then the laser beam is easily conducted into the scanner system.

In a turbine scanner according to be employed according to an embodiment of the invention (FIG. 4) the mirrors 21 to 28 can deviate from each other in such a manner that during one round of rotational movement there are scanned as many line-shaped areas (FIG. 5) 29 as there are mirrors 21 to 28.

In one preferred embodiment of the invention laser ablation is carried out under vacuum under a vacuum of at least $10^{-5}$ mbar, preferably at least $10^{-4}$ mbar and most preferably at least $10^{-2}$ mbar. High vacuum conditions require quite long pumping times, and thus prolonged production times of coatings.

According to the invention it is possible to conduct the coating in a manner wherein the distance between the target material and said uniform surface area to be coated is under 25 cm, preferably under 15 cm and most preferably under 10 cm. This accomplishes the development of coating chambers with drastically diminished volumes, making the overall price of coating production lines lower and decreasing further the time required for vacuum pumping.

In a preferred embodiment of the invention the ablated surface of said target material can be repeatedly ablated in order to produce defect-free coating. In case of most of the present coating technologies, the target material wears unevenly in a manner that the affected area cannot be reused for ablation and must thus be either discarded or sent for regeneration after certain use. The problem has been tackled by developing different techniques for feeding constantly new, non-ablated target surface for coating purposes by for example moving the target material in x/y-axis or by rotating a cylinder-formed target material. The present invention accomplishes simultaneously excellent coating properties and production rates as well as use of target material in a way wherein the good quality plasma retains its quality throughout the use of substantially whole piece of target material. Preferably, more than 50% of the single target material weight is consumed to production of good quality plasma according to the invention. With good quality plasma is hear meant plasma for producing defect-free coatings and thinfilms, the high quality of plasma plume being maintained at high pulse frequencies and deposition rates. Some of such properties are described here below.

According to one embodiment of the invention, the average surface roughness of produced articulating coating on said uniform surface area is less than 100 nm as scanned from an area of 1 µm² with Atomic Force Microscope (AFM). More preferably, the average surface roughness is less than 30 nm. With average surface roughness is here meant the average deviation from the centre line average curve fitted by a proper procedure, such as those available in AFM or profilemeter. The surface roughness affects amongst the other the wear- and scratch-free properties, tribological properties as well as the transparency of coating on metal products coated according to the invention.

In another embodiment of the invention, produced coating on said uniform surface area contains less than one pinhole per 1 mm², preferably less than one pinhole per 1 cm² and most preferably no pinholes at said uniform surface area. Pinhole is a hole going through or substantially through the coating. Pinholes provide a platform for erosion of the originally coated material for example by chemical or environmental factors. Single pinhole in for instance coating of which ever medical product leads easily to dramatically lowered life-time of said product.

The medical product itself can comprise virtually whichever metal, metal compound such as metal alloys, oxides, carbides, nitrides or composite materials of these.

According to one embodiment of invention, said articulating surface of the medical product is coated with only one single coating. According to another embodiment of the invention, said articulating surface of the medical product is coated with multilayered coating. Several coatings can be produced in for different reasons. One reason might be to enhance the adhesion of certain coatings to metal product surfaced by manufacturing a first set of coating having better adhesion to metal surface and possessing such properties that the following coating layer has better adhesion to said layer than to metal surface itself. Additionally, the multilayered coating can possess several functions not achievable without said structure. The present invention accomplishes the production of several coatings in one single coating chamber or in the adjacent chambers.

The present invention further accomplishes the production of composite coatings to articulating surface of the medical product by ablating simultaneously one composite material target or two or more target materials comprising one or more substances.

The coating thicknesses must not be limited to those, because the present invention accomplishes the preparation of molecular scale coatings on the other hand, very thick coatings such as 100 µm and over, on the other hand.

The present invention further accomplishes the preparation of 3D-structures for medical use by employing certain desired component as a scaffold for growing said 3D-structure. According to the invention there is also provided a medical product comprising an articulating surface coated with ultra short pulsed laser deposition wherein the articulating surface of the medical product contains less than one pinhole per 1 mm².

Preferably, the product contains less than one pinhole per 1 mm² and most preferably no pinholes at the articulating surface coating. In one preferred embodiment of the invention, such articulating surface of the medical product is coated with metal, metal oxide, metal nitride, metal carbide or mixtures of these.

In a second preferred embodiment of the invention, such articulating surface of the medical product is coated with carbon material comprising over 90 atomic-% of carbon, with more than 70% of $sp^3$-bonding.

In still another preferred embodiment of the invention, such articulating surface of the medical product is coated with material comprising carbon, nitrogen and/or boron in different ratios.

According to the invention, the coating thickness is at least 1 μm, preferably 10 μm to 20 μm. It can also be 100 μm.

According to still another embodiment of the invention, articulating surface of the medical product is coated in a manner wherein the first 50% of the produced articulating surface layer does not contain any particles having a diameter exceeding 1000 nm, preferably 100 nm and most preferably 30 nm. It is also preferable, that the average surface roughness of articulating surface layer is less than 100 nm as scanned from an area of 1 μm² with Atomic Force Microscope (AFM). With average surface roughness is here meant the average deviation from the centre line average curve fitted by a proper procedure, such as those available in AFM or profilemeter.

Example to Demonstate Known Art Problems—Laser Technology

Plasma related quality problems are demonstrated in FIGS. 15a and 15b, which indicate plasma generation according to known techniques. A laser pulse □ 1114 hits a target surface 1111. As the pulse is a long pulse, the depth h and the beam diameter d are of the same magnitude, as the heat of the pulse 1114 also heat the surface at the hit spot area, but also beneath the surface 1111 in deeper than the depth h. The structure experiences thermal shock and tensions are building, which while breaking, produce fragments illustrated F. As the plasma may be in the example quite poor in quality, there appears to be also molecules and clusters of them indicate by the small dots 1115, as in the relation to the reference by the numeral 1115 for the nuclei or clusters of similar structures, as formed from the gases 1116 demonstrated in the FIG. 15b. The letter "o"s demonstrate particles that can form and grow from the gases and/or via agglomeration. The released fragments may also grow by condensation and/or agglomeration, which is indicated by the curved arrows from the dots to Fs and from the os to the Fs. Curved arrows indicate also phase transitions from plasma 1113 to gas 1116 and further to particles 1115 and increased particles 1117 in size. As the ablation plume in FIG. 15b can comprise fragments F as well as particles built of the vapours and gases, because of the bad plasma production, the plasma is not continuous as plasma region, and thus variation of the quality may be met within a single pulse plume. Because of defects in composition and/or structure beneath the deepness h as well as the resulting variations of the deepness (FIG. 15a), the target surface 1111 in FIG. 15b is not any more available for a further ablations, and the target is wasted, although there were some material available.

Such problems are common with nanosecond-lasers in general, and present pico-second lasers, if they were employing the state of the art scanners.

Example of Invention—1

FIG. 13a demonstrates a target material ablated with pico-second-range pulsed laser employing rotating scanner with speed accomplishing the ablation of target material with slight overlapping of adjacent pulses, avoiding the problems associated with prior art galvano-scanners. FIG. 13b shows enlarged picture of one part of the ablated material, clearly demonstrating the smooth and controlled ablation of material on both x- and y-axis and thus, generation of high quality, particle-free plasma and further, high quality thin-films and coatings. FIG. 13c demonstrates one example of possible x- and y-dimensions of one single ablation spot achieved by one or few pulses. Here, it can be clearly seen, that the invention accomplishes the ablation of material in a manner wherein the width of the ablated spot is always much bigger than the depth of the ablated spot area. Theoretically, the possible particles (if they would be generated) could now have a maximum size of the spot depth. The rotating scanner now accomplishes the production of good quality, particle free plasma with great production rate, with simultaneously large scanning width, especially beneficial for substrates comprising large surface areas to be coated. Furthermore, the FIGS. 13a, 13b and 13c clearly demonstrate that opposite to present techniques, the already ablated target material area can be ablated for new generation of high class plasma—reducing thus radically the overall coating/thin-film producing cost.

Example of Invention—2

FIG. 14 demonstrates an example wherein coating is carried out by employing a pico-second USPLD-laser and scanning the laser pulses with turbine scanner. Here, the scanning speed is 30 m/s, the laser spot-width being 30 μm. In this example, there is an ⅓ overlapping between the adjacent pulses.

Examples of Invention—Coated Products

None of the prepared coating samples contained any pinholes due to deposition on examines surfaces of prepared coatings. Some of the samples were produced by employing state of the art galvano-scanners, some by employing rotating turbine scanner. When employing turbine scanner, pulse repetition rates exceeding 1 MHz could be employed.

Example 1

Ceramic Coatings for Different Kind of Materials

Different kind of materials can be utilized in medical applications: metals, ceramics, polymers and composites. In this example, examples from different material groups were selected including silicon, Ta, Ti, stainless steel, CoCrMo, alumina, glass, polycarbonate, polyimide and polyethylene. Samples had a polished, nearly a mirror-line surface finish. They were washed with acetone and ethanol. The samples were loaded in a vacuum chamber and pumped down to a vacuum better than $10^{-4}$ mbar. Then they were coated with a ceramic coating using an ultra short pulse laser ablation. Fiber laser gave a 15-20 ps pulse with a frequency in range 1-4 MHz. A single pulse energy was varied in the range 0-5 μJ and the laser spot was focused by proper lenses in a diameter in the range 10-40 μm depending on the case. The ceramic target materials included titania, yttria stabilized zirconia (Y—$ZrO_2$), yttria/alumina (YAG), alumina/titania (ATO), graphite and $C_3N_4H_x$ (Carbodeon Ltd). In each case, first the pulse energy was increased to find out the ablation threshold of each material (for example about 0.5 J/cm² for titania and graphite). Then the pulse energy was typically increased 40-100% to obtain a stable plasma plume suitable for deposition. Proper parameters were selected based on the preliminary tests with each setup. In each case a coating thickness was varied typically in the range 50-1000 nm. Furthermore, a set of substrates with different roughnesses <10 nm (mirror), 100 nm (matt), 1000 nm (rough) and >1 μm (very rough) were prepared and coated. In addition, surfaces with polymer lithography patterns were coated.

It turned out that all the mentioned coating materials could be efficiently deposited by using ultra short pulse laser deposition. The adhesion of the films was good even on roughened surfaces and the coatings couldn't be delaminated by a scotch tape test or a simple scratch test. The surfaces were imaged using ESEM and AFM. Typically the average surface roughness $R_a$ was better than 10 nm. As an example FIG. 2a shows the AFM image for a relatively thick (500 nm) AD (amorphous diamond) coating with a surface roughness of 8 nm. The surface of the coating as imaged by ESEM (FIG. 2b) looks very smooth and practically featureless. Surprisingly just a few nanometer range particles appeared and no macroparticles due to coating process were observed. This leads to good behavior in corrosion tests using strong acids, because coatings didn't have open corrosion pathways. In these tests, a drop of strong acid such as HF, $HNO_3$, $H_2SO_4$ or their mixture is applied on the coatings and the behavior is monitored visually or with an optical microscope. In high quality coating, no gas bubble formation is observable and acid drop is simply slowly evaporating out.

Mechanical properties of the coatings were tested using a pin-on-disk tester with alumina and hardened steel balls 6 mm in diameter and loads in the range 10-500 g and total number of rounds in range 100-100 000 with a wear track of 4-6 mm in diameter Hard oxide and amorphous diamond coatings turned out to be very wear resistant with very low wear rates, typical for ceramic coatings.

Example 2

Metallic Coatings from Medical Metals or Alloys

In medical applications, typical metals utilized include biocompatible Ti and its alloys, stainless steel, tantalum, platinum and other precious metals. CoCr based alloys are common, but they were omitted in these tests due to toxic components (Co and Cr). All these metals can be used as a source for ultra short pulse laser deposition. In this test titanium and tantalum were deposited in the same way as explained in example 1. High purity materials (purity better than 99.9%) were used as a target. These metals can be ablated with a relative low fluence (e.g. Ti was deposited with a fluence of 0.7-1.0 $J/cm^2$). Coatings were highly adherent and extremely smooth when studied with AFM and ESEM. These kinds of high quality metal coatings can be applied as such or as an intermediate layer under ceramic coatings. The composition of the coatings was found out to be very close to that of the target materials by EDS measurement. In general, compositional stability of coating with optimal deposition parameters has turned out to be a very advantageous feature of the invention described here.

Example 3

Metal Oxide Coatings Using Metal Targets and Reactive Oxidation

Reactive evaporation can be utilized also with ultra short pulse laser ablation. In these tests, as a comparison some metal oxides were deposited using the same procedure as in the examples above, except by utilizing reactive oxygen atmosphere of $5 \times 10^{-1}$-$10^{-3}$ mbar and metallic targets. Optimal gas atmosphere was selected based on the oxide transparency, i.e. to maximize visual transparency. Metallic targets can be easily obtained in plate, foil or rod form. Ti and different commercial Al-alloys such as EN 2024, EN5754, EN6082 and EN 7075 were used as targets. Furthermore, Al/Ti metallic target with different compositions of 3.0, 8.4, 10.3 and 16.6 wt. % Ti (Al balance) were processed from high purity (>99.9%) powders of these metals. Mixed powders were first compressed in pellets with a diameter of 13 mm, then sintered at temperatures of 740 C and finally polished to obtain smooth flat targets.

Very smooth $TiO_2$ oxide coatings were obtained on metal, ceramic and polymer substrates by the procedure described above at an oxygen pressure of $10^{-1}$ mbar and fluence 0.7 $J/cm^2$. The average surface roughness was 0.2 nm for a 100 nm thick film (FIG. 9 a+b).

Using the same procedure Al/8.4 wt. % Ti target was used to deposit hard oxide coatings on metal, ceramic and polymer substrates. Their properties like transparency and wear resistance turned out to correspond quite well with the similar coatings deposited using a ceramic $Al_2O_3/TiO_2$ (ATO) target. Already based on these examples it is evident that metal targets and oxidizing atmosphere provides an efficient route to produce single and multi component oxides for medical applications even on large scale and large areas.

Example 4

Bone Screws

Figure 10:
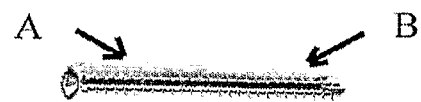

This example demonstrates the possibility to apply coatings on products with a complicated shape such as bone screws, hip and knee implants. Cortical bone screws made of stainless steel with a diameter of 2.7 and 3.5 mm were used in this example. They were coated with amorphous diamond by ablating graphite with pulse repetition rate of 1 MHz, pulse energy 4 µJ, pulse length 15 ps and the distance between the target material and surface to be coated was 5 mm. The vacuum level was $10^{-5}$ atmospheres during the coating process. In this case two directions of the plume were utilized to apply optimized coating as schematically illustrated in FIG. 10. The average surface roughness determined on a reference sample was about 5 nm as scanned from an area of 1 $\mu m^2$ with Atomic Force Microscope (AFM). No pinholes were found on any measured area of diamond coating and its adhesion was good. The carbon content was measured to be above 98% and the degree of $sp^3$-bonding was over 70%.

Figure 11:
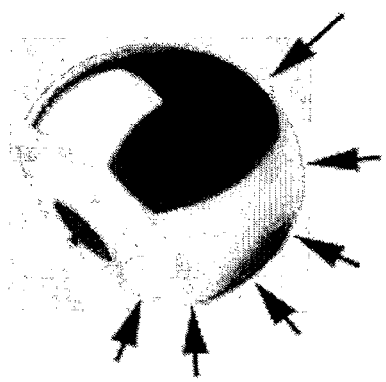
Figure 12:
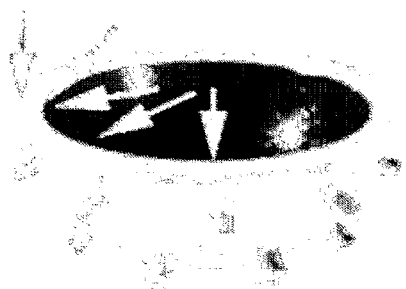

It should be noticed that optimal deposition geometries can be easily achieved by manipulating sample in ultra short pulse laser ablation deposition as described here. Normally optimal angle for deposition is perpendicular to the surface. In the case of a screw two plume directions were sufficient to provide high quality and adherent coating. In a similar manner more complicated implants and instruments can be deposited using very short target-to-sample distances and several deposition directions as shown in FIG. 11 for a hip joint ball and in FIG. 12 for a hip joint cup. An optimal geometry is a special advantage of this method with small pen-shaped depositing plasma plume at short target-to-sample distances.

Based on these examples it is obvious for the skilled men in the art that different kinds of coatings can be applied by the same technique including metals, oxides, nitrides, carbides as well as depositing on different solid materials or products made of them. The shapes of the products may vary a lot as far as the surface to be coated can be accessed by a small size beam.

The invention claimed is:

1. A method for coating a certain surface of a medical product, comprising coating said surface of the medical product with plasma generated by ablation of a target material by employing ultra short pulsed laser beam deposition, wherein the laser beam is scanned at a pulse frequency of at least 1 MHz, wherein the ultra short pulse has a pulse length of less than 50 ps, and wherein the laser beam has a scanning velocity at the surface of the target material of more than 10 m/s to generate said plasma.

2. The method according to claim 1, wherein said surface of the medical product is coated with material containing at least one of following materials or a mixture of these:
   metal, metal oxide, metal nitride, and/or metal carbide; or
   carbon, nitrogen and/or boron; or
   carbon material comprising over 90 atomic-% of carbon, with more than 70% of $sp^3$-bonding.

3. The method according to claim 1, wherein said surface of the medical product is coated with a multilayered coating.

4. The method according to claim 1, wherein the coating thickness is at least 1 μm.

5. The method according to claim 1, wherein said surface of the medical product contains less than one pinhole per 1 $mm^2$ at the surface of the medical product.

6. The method according to claim 1, wherein said surface of the medical product is coated in a manner wherein the first 50% of the produced surface layer does not contain any particles having a diameter exceeding 1000 nm.

7. The method according to claim 1, wherein the average surface roughness of produced articulating surface layer is less than 100 nm as scanned from an area of 1 $μm^2$ with Atomic Force Microscope (AFM).

8. The method according to claim 1, wherein the pulsed laser beam is scanned with a rotating optical scanner comprising at least one mirror for reflecting said laser beam.

9. The method according to claim 1, wherein the laser ablation is performed under a vacuum of at least $10^{-5}$ mbar.

* * * * *

UNITED STATES PATENT AND TRADEMARK OFFICE
CERTIFICATE OF CORRECTION

PATENT NO. : 8,486,073 B2  Page 1 of 1
APPLICATION NO. : 12/280609
DATED : July 16, 2013
INVENTOR(S) : Lappalainen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1188 days.

Signed and Sealed this
Eighth Day of September, 2015

Michelle K. Lee
*Director of the United States Patent and Trademark Office*